United States Patent
Malik et al.

(10) Patent No.: US 10,433,818 B2
(45) Date of Patent: Oct. 8, 2019

(54) COLOR CODING AN IMAGE FOR IDENTIFYING ANATOMY USING QUANTITATIVE TRANSMISSION ULTRASOUND TOMOGRAPHY

(71) Applicant: QT Ultrasound LLC, Novato, CA (US)

(72) Inventors: Bilal Hameed Malik, Novato, CA (US); John Charles Klock, Nicasio, CA (US); James W. Wiskin, Novato, CA (US); Nasser Charles Pirshafiey, Thousand Oaks, CA (US); Mark Wayne Lenox, College Station, TX (US)

(73) Assignee: QT ULTRASOUND LLC, Novato, CA (US)

( * ) Notice: Subject to any disclaimer, the term of this patent is extended or adjusted under 35 U.S.C. 154(b) by 186 days.

(21) Appl. No.: 15/836,576

(22) Filed: Dec. 8, 2017

(65) Prior Publication Data
US 2019/0053789 A1     Feb. 21, 2019

Related U.S. Application Data

(60) Provisional application No. 62/546,898, filed on Aug. 17, 2017.

(51) Int. Cl.
| | | |
|---|---|---|
| *A61B 8/08* | (2006.01) | |
| *A61B 8/14* | (2006.01) | |
| *G06T 7/00* | (2017.01) | |
| *G06K 9/62* | (2006.01) | |
| *G06T 7/60* | (2017.01) | |
| *G06T 11/60* | (2006.01) | |
| *A61B 8/15* | (2006.01) | |
| *A61B 8/00* | (2006.01) | |

(52) U.S. Cl.
CPC .......... *A61B 8/5223* (2013.01); *A61B 8/0825* (2013.01); *A61B 8/14* (2013.01); *A61B 8/5246* (2013.01); *G06K 9/6269* (2013.01); *G06T 7/0014* (2013.01); *G06T 7/60* (2013.01); *G06T 11/60* (2013.01); *A61B 8/15* (2013.01); *A61B 8/463* (2013.01); *G06K 9/6256* (2013.01); *G06T 2207/10024* (2013.01); *G06T 2207/10132* (2013.01); *G06T 2207/30068* (2013.01); *G06T 2210/41* (2013.01)

(58) Field of Classification Search
CPC .......... A61B 8/0825; A61B 8/14; A61B 8/15; A61B 8/463; A61B 8/5223; A61B 8/5246; G06K 9/6256; G06K 9/6269; G06T 11/60; G06T 2207/10024; G06T 2207/10132; G06T 2207/30068; G06T 2210/41; G06T 7/0014; G06T 7/60
See application file for complete search history.

(56) References Cited

U.S. PATENT DOCUMENTS

| | | | |
|---|---|---|---|
| 2015/0209012 A1* | 7/2015 | Oh ........................ | A61B 8/465 600/438 |
| 2016/0030005 A1* | 2/2016 | Kulakowski, Jr. ... | A61B 8/4444 600/438 |

* cited by examiner

*Primary Examiner* — Manuchehr Rahmjoo
(74) *Attorney, Agent, or Firm* — Talem IP Law, LLP

(57) ABSTRACT

The speed of sound, attenuation, and reflection data obtained through quantitative Transmission ultrasound (QTUS) differs by body tissue type. Skin, fat, gland, duct and connective tissues can be classified based on the sound, attenuation, and reflection data. The system can assign coloration to breast images to provide a color-coded breast tissue volume based on the output of the classifier.

17 Claims, 18 Drawing Sheets

| Pair | | p-value | | |
|---|---|---|---|---|
| | | Reflection | Speed of Sound | Attenuation |
| Skin | fat | < 0.0001 | < 0.0001 | < 0.0001 |
| Skin | glands | < 0.0001 | 0.1597 | < 0.0001 |
| Skin | ducts | < 0.0001 | < 0.0001 | < 0.0001 |
| Glands | fat | < 0.0001 | < 0.0001 | 0.0058 |
| Glands | ducts | 0.5379 | < 0.0001 | 0.049 |
| Fat | ducts | < 0.0001 | < 0.0001 | 0.2943 |
| Skin | Coopers | < 0.0001 | < 0.0001 | 0.0005 |
| Ducts | Coopers | < 0.0001 | < 0.0001 | < 0.0001 |
| Glands | Coopers | < 0.0001 | < 0.0001 | < 0.0001 |
| Fat | Coopers | < 0.0001 | < 0.0001 | 0.0007 |

FIG. 8

| True class | Coopers | ducts | fat | glands | skin |
|---|---|---|---|---|---|
| Coopers | 92 | | 3 | 2 | 2 |
| ducts | 4 | 72 | | 12 | 11 |
| fat | 3 | | 94 | 1 | |
| glands | 1 | 1 | | 77 | 20 |
| skin | | 5 | | 9 | 85 |

Predicted class

FIG. 9A

COLOR CODING AN IMAGE FOR IDENTIFYING ANATOMY USING QUANTITATIVE TRANSMISSION ULTRASOUND TOMOGRAPHY

CROSS-REFERENCE TO RELATED APPLICATION

The present invention claims the benefit of U.S. Provisional Application Ser. 62/546,898, filed on Aug. 17, 2017, which is hereby incorporated by reference in its entirety, including any figures, tables, and drawings.

BACKGROUND

Computer-aided detection/diagnosis (CAD) systems have shown significant potential towards reading image volumes more efficiently. A common theme and basis of CAD methods is image segmentation and classification. Many established methods built on image intensity based and/or shape based parameters, have been used to perform such analyses. The classification problem is typically solved using machine-learning methods, which can be either supervised or unsupervised.

While a goal of breast imaging CAD systems is to detect and classify pathological findings, an important initial step is to classify normal breast tissue types, which can potentially serve to improve the specificity of tumor detection.

BRIEF SUMMARY

Techniques and systems for the detection and determination of tissue types are described.

Speed of sound (SOS), attenuation and reflection images obtained through quantitative transmission ultrasound (QTUS) can be used to detect and determine a tissue type as, for example, skin, fat, gland, duct, or connective tissue. Coloration of pixels in an image can be performed according to the determination of a tissue type. Once calibrated, the QTUS image parameters can generate whole breast image volumes classified into the aforementioned tissue types.

A computer-implemented method for tissue type identification can include evaluating image data from a quantitative transmission ultrasound system to assign a color to each pixel registration, the image data including at least a speed of sound image and a reflection image. The computer-implemented method further includes distinguishing between any pair of tissue types using speed of sound and reflection data. The distinguishing process for connective tissue, such as ligaments, and fat can separate pixels as probable connective tissue or probable fat from probable ducts and probable glands by the speed of sound data from the speed of sound image; and can separate pixels as probable connective tissue from probable fat by the reflection data from the reflection image since connective tissue and fat have speed of sound values smaller than that of ducts and glands and the connective tissue have reflection values greater than that of fat. Each pixel is stored having a color parameter indicating the assigned color for its probable tissue type. In response to a request to display a particular tissue type, pixels stored associated with the corresponding color parameter for the particular tissue type are identified and those pixels displayed with the assigned color from the stored color parameter for the particular tissue type in a view screen. In addition to color coding, the particular tissue or tissues can be isolated based on type or color for better visualization of their shape, size and location.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 8 shows a table of the results of a non-parametric Mann-Whitney U Test.

FIG. 9A shows a confusion matrix for five tissue types.

DETAILED DISCLOSURE

Quantitative Transmission Ultrasound (QTUS) techniques and systems are provided for the detection and determination of body tissue types. In certain implementations, QTUS uses ultrasound energy to image and characterize breast tissue.

Machine learning can be used to classify the QTUS images. Image texture features, such as pixel value, first order statistics (mean, central moments, etc.), second order statistics (contrast, correlation, entropy, etc.) can be derived from co-registered speed of sound, attenuation and reflection images, and can be used as feature vectors to classify normal breast tissue types: glands, ducts, fat, skin and connective tissue. The classifier can then be used to provide a color-coded classification of whole breast QTUS image volumes.

A QTUS system performs both reflection and transmission ultrasound methods to gather data. The reflection portion directs pulses of sound wave energy into tissues and receives the reflected energy from those pulses—hence it is referred to as "reflection ultrasound." Detection of the sound pulse energies on the opposite side of a tissue after it has passed through the tissue is referred to as "transmission ultrasound."

In particular, QTUS uses inverse scatter technology providing transmission information (speed of sound and attenuation) mapping of breast tissue. The speed of sound map, which is essentially related to a map of refractive index values, is then used for refraction correction in the reflection image.

QTUS enables evaluation of tissue in clinical ultrasound by offering high spatial and contrast resolution, with absolute spatial registration (no image warping or stretching) quantitative imaging. Advantageously, the resulting images can be used to distinguish tissue types, which can be, consequently, useful in the detection of breast cancer.

Figure 1:
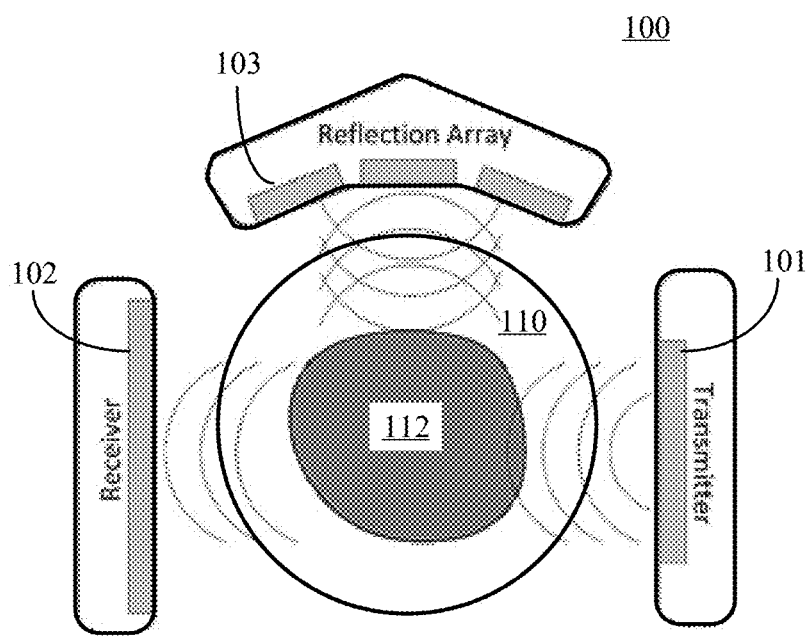
FIG. 1 illustrates a topography of a Quantitative Transmission Ultrasound (QTUS) system.

FIG. 1 illustrates a topography of a QTUS system. Referring to FIG. 1, the imaging portion of the QTUS system 100 can include a transmitter 101, receiver 102, and transducer 103. A receptacle 110 is provided to present a water (or other liquid or gel) bath in which a patient may rest at least the region of interest (e.g., the part 112 being imaged). The motion artifact associated with patient movement can affect the image quality. In some embodiments, an adhesive pad with a magnet can be placed near the nipple region of the breast and docked to a magnetized retention rod that gently holds the breast in a consistent position during the scan. In some cases, a membrane over the bath between the breast and the liquid is used to hold the breast (and allow for alternative liquids in the bath).

The transmitter 101 and a receiver 102 are provided on opposite sides so that the receiver 102 is placed to perform transmission ultrasound. The transmitter 101 and the receiver 102 may be in the form of an array of transmitters and receivers. The transmitter array emits broad-band plane pulses (e.g., 0.3-2 MHz) while the receiver array includes elements that digitize the time signal. A set of reflection transducers 103 are also included to perform reflection measurements. The reflection transducers 103 can include transducers of varying focal lengths, providing a large depth of focus when combined. The reflection imaging provides images that represent propensity for reflection information (impedance mismatch) spatially. The reflection images can be refraction-corrected and attenuation-calibrated using the speed of sound and attenuation information acquired from the transmission data.

360° of data can be obtained through rotation of the system. The system (particularly arms containing the transmitter 101 and the receiver 102) may rotate 360° to acquire measurements from effectively all the angles (e.g., data sufficient to provide a 360° view even if not taken at every angle between 0° and 360°) and collect tomographic views of ultrasound wave data. The reflection transducer data can be collected with one or more horizontal reflection transducers 103 that acquire data in steps or continuously as they rotate 360° along with the transmitter 101 and receiver 102.

In a specific implementation, the system rotates around the patient while both transmission and reflection information are captured. It is not necessary to acquire an entire 360° scan; images can be reconstructed with limited information. For example, a patient can lie prone with their breast pendent in a controlled temperature water bath (e.g., 31° C.) within the field of view of the transmitter 101, receiver 102, and transducer 103 as the transmitter 101, receiver 102, and transducer 103 rotate 360° around the patient. Then, in one example case 180 projections of ultrasound wave data may be obtained. In another example case, 200 to up to 360 projections of the ultrasound wave data may be obtained.

Other detector configurations may be used. For example, additional detectors in a continuous or discontinuous ring or polygon configurations may be used. Of course, any configuration selected will have tradeoffs in speed and cost. In addition, in some cases, reflection arrays (the transducers for the reflection measurements) can do double-duty and perform independent transmission and receiver functions as well as reflection measurements.

In some embodiments, the acquired reflection images are spatially compounded and corrected for refraction using the corresponding speed of sound information. The spatial compounding results in significant reduction of image speckle while maintaining the high resolution nature of the images similar to that of traditional B-mode ultrasound. In another embodiment, the end result of each scan may be a 3D volume of essentially three different modalities: speed of sound, attenuation, and reflection. Each of these 3D volume images may be consist of voxels chosen from a range of sizes. For example, in one embodiment a voxel may have dimensions of 400 μm×400 μm×1 mm.

Figure 2:
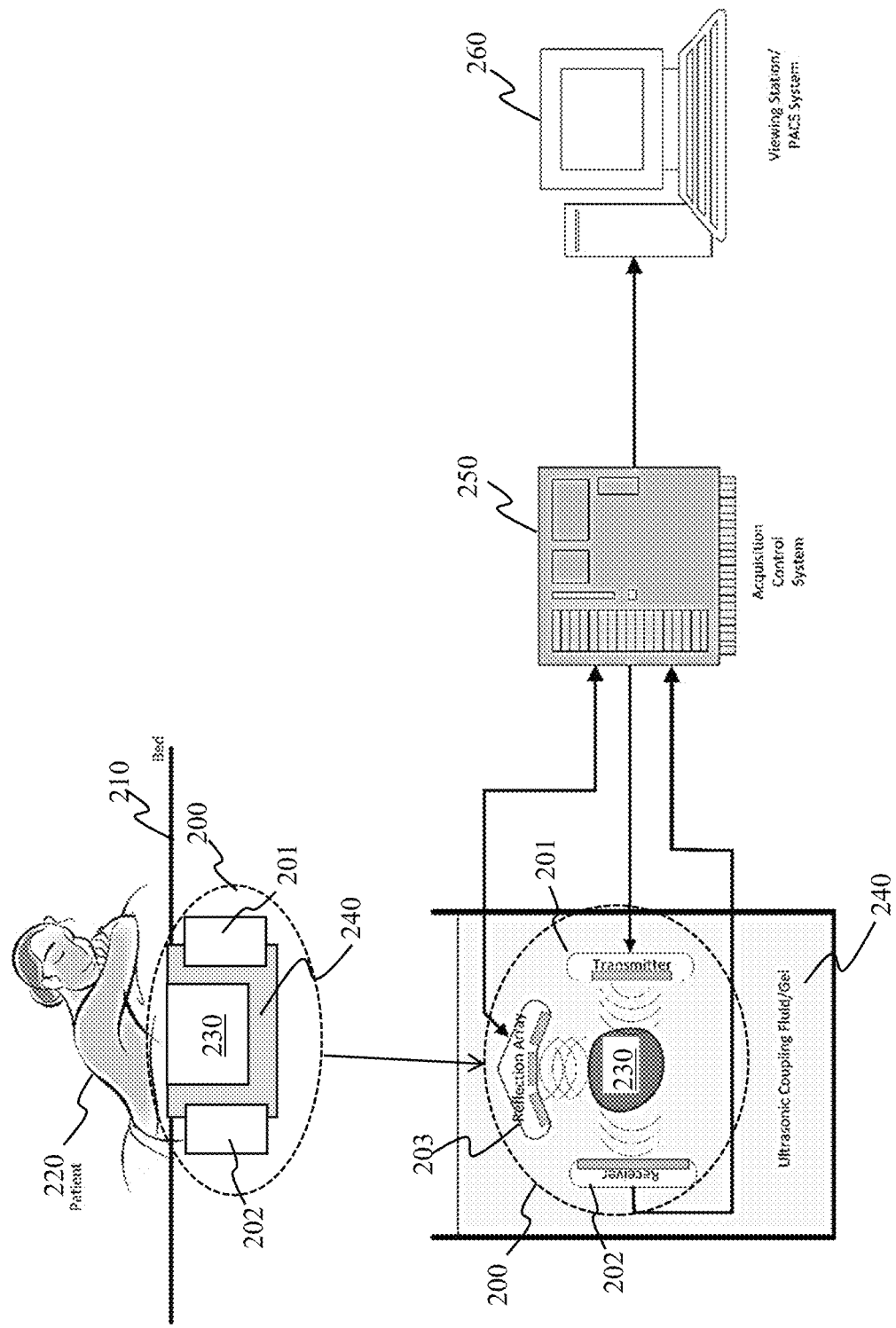
FIG. 2 illustrates a system environment.

FIG. 2 illustrates a system environment. Referring to FIG. 2, active components (e.g., the imaging components, or transducers, of a QTUS system 200), such as a transmitter 201, receiver 202, and reflection array 203, can be disposed around a receptacle 230 beneath a bed 210 on which a patient 220 can lie. The patient 220 can be scanned in the prone position, resulting in a comfortable procedure. Other configurations are also possible for the apparatus on which the patient is positioned.

The active components (transducers of QTUS system 200) are arranged so that data may be obtained 360° around the receptacle 230 in the bed 210 (via any suitable configuration; and are coupled to the patient with an ultrasonic coupling medium 240 (fluid or gel), at least some of which is disposed in the receptacle 230. An acquisition control system 250 operates the various active components (e.g., the transducers) and can control their physical motion (when system 200 is arranged in a rotating configuration).

The acquisition control system 250 can automate a scan in response to a start signal from an operator. This automated acquisition process does not require operator interaction during the scanning procedure. Once the scan is complete, the acquisition control system 250 (or other computing system having access to the data) can compute the reflection, speed of sound, and attenuation results from the collected data. The acquisition protocol enables temporal comparisons of 3D data sets; and these data sets can be compared in the same plane and orientation as those acquired with other 3D modalities, such as magnetic resonance imaging (MRI). The acquisition control system 250 can transmit the results to a viewing station 260 and/or a picture archival and communication system (PACS). Thus, images can be automatically acquired, stored for processing, and available for physician review and interpretation at the review workstation 260.

Figure 3:
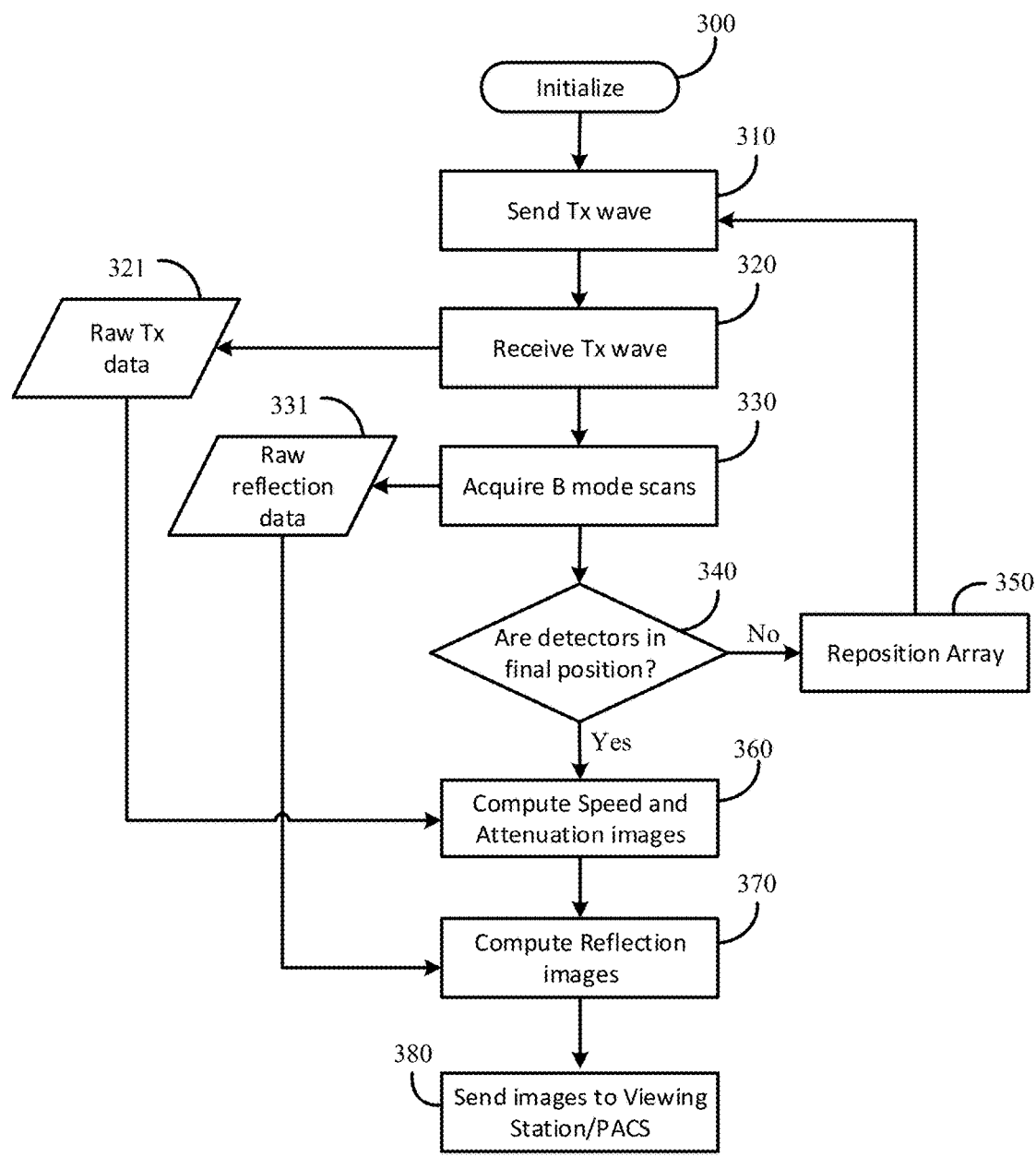
FIG. 3 illustrates a process flow diagram of a process that can be carried out by an acquisition control system.

FIG. 3 illustrates a process flow diagram of a process that can be carried out by an acquisition control system. In response to receiving an indication to initiate automated scanning (e.g., from an operator), an acquisition control system, such as system 250, can initialize (300) and send a transmission wave from a specified angle about a patient (310), for example from one or more transmitters (such as transmitter 201). As the receiver(s) 202 sense the signal transmitting through the patient (320), raw transmission data 321 is captured. Then, spatially compounded extended depth of focus B mode scans, for example using transceivers 203, are acquired (330) to obtain raw reflection data 331. Of course, in some cases, the B mode scans may be performed before the transmission ones. Additionally, in some embodiments reflection transducers may have different focal lengths to extend the overall depth of focus within the imaging volume.

The acquisition control system determines whether the detectors are in the final position (340). For a rotating system, the acquisition control system can communicate with a motor control of the platform on which the active components are provided so that a current and/or next position of the platform is known and able to be actuated. For a fixed system, the acquisition control system determines the selection of the active arrays according to an activation program. Accordingly, the "detection" of final position may be based on information provided by the motor control, position sensors, and/or a position program (e.g., using counter to determine whether appropriate number of scans have been carried out or following a predetermined pattern for activating transceivers). If the detectors are not in final position, the acquisition control system causes the array to be repositioned (350), for example, by causing the platform to rotate or by selecting an appropriate array of transceivers of a fixed platform configuration. After the array is repositioned, the transmission wave is sent (310) and received (320) so that the raw transmission data 321 is collected and the B mode scans can be acquired (330) for raw reflection data 531. This repeats until the detectors are determined to be in the final position.

Once all the data is collected (and the detectors completed the final position), speed of sound images, attenuation images, and reflection images can be computed (360). Reflection images may be corrected for refraction with the aid of the speed of sound images. In some cases, both the original uncorrected reflection images and the refraction corrected reflection images may be available and sent to a viewing station and/or PACS (e.g., systems 260 of FIG. 2) (380). The computations may be carried out according to methods described, for example, in U.S. Pat. Nos. 5,588,032; 6,005,916; 6,587,540; 6,636,584; 7,570,742; 7,684,846; 7,841,982; and 8,246,543, each of which are incorporated by reference in their entirety except for anything inconsistent with the subject specification.

The refraction corrected reflection, speed of sound, and attenuation images, from these systems or other systems from which reflection, speed of sound, and attenuation image data can be acquired, can be used to determine the type of breast tissue traversed. In one embodiment, data from one or a combination of reflection, speed of sound, and attenuation images may be used to determine criteria which will be associated with a particular tissue type. In another embodiment, data from one or a combination of these images may be used to determine a set of characteristics for a pixel, or voxel, of an image to compare to the criteria associated with a particular tissue type.

A color can be assigned to each type of breast tissue. The information about the type of breast tissue, in combination with additional parameters, such as surface-to-volume ratio and doubling time, provides more accurate, specific information regarding a breast tissue type, thus improving the ability to detect and classify possible abnormalities, potentially decreasing unnecessary biopsies.

Figure 4A:
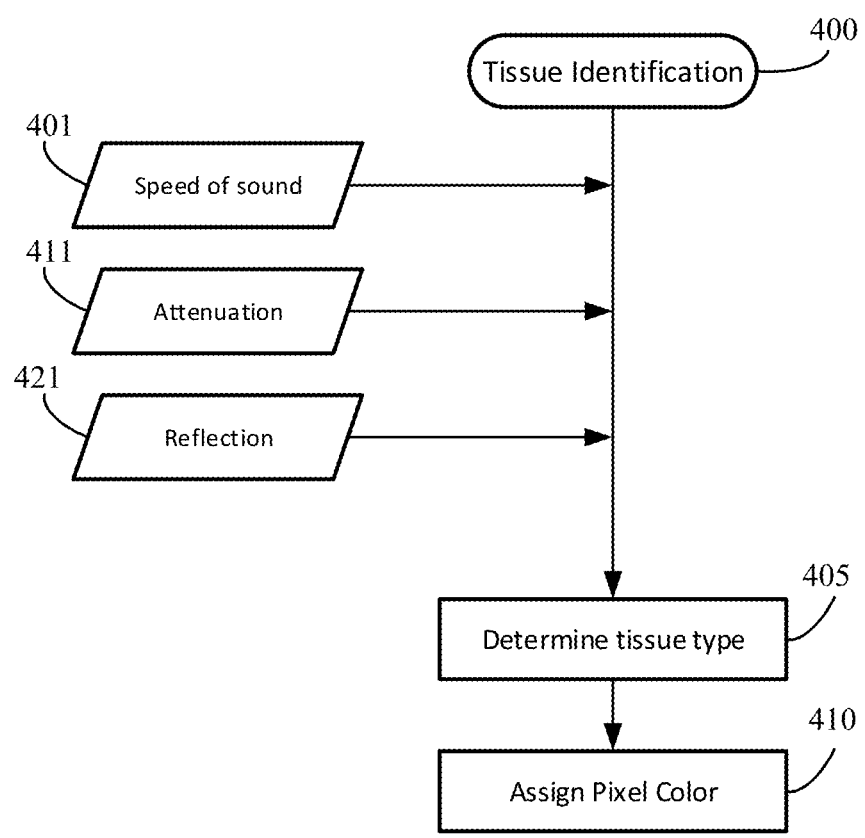
FIG. 4A illustrates a general process flow for tissue type identification.
Figure 4B:
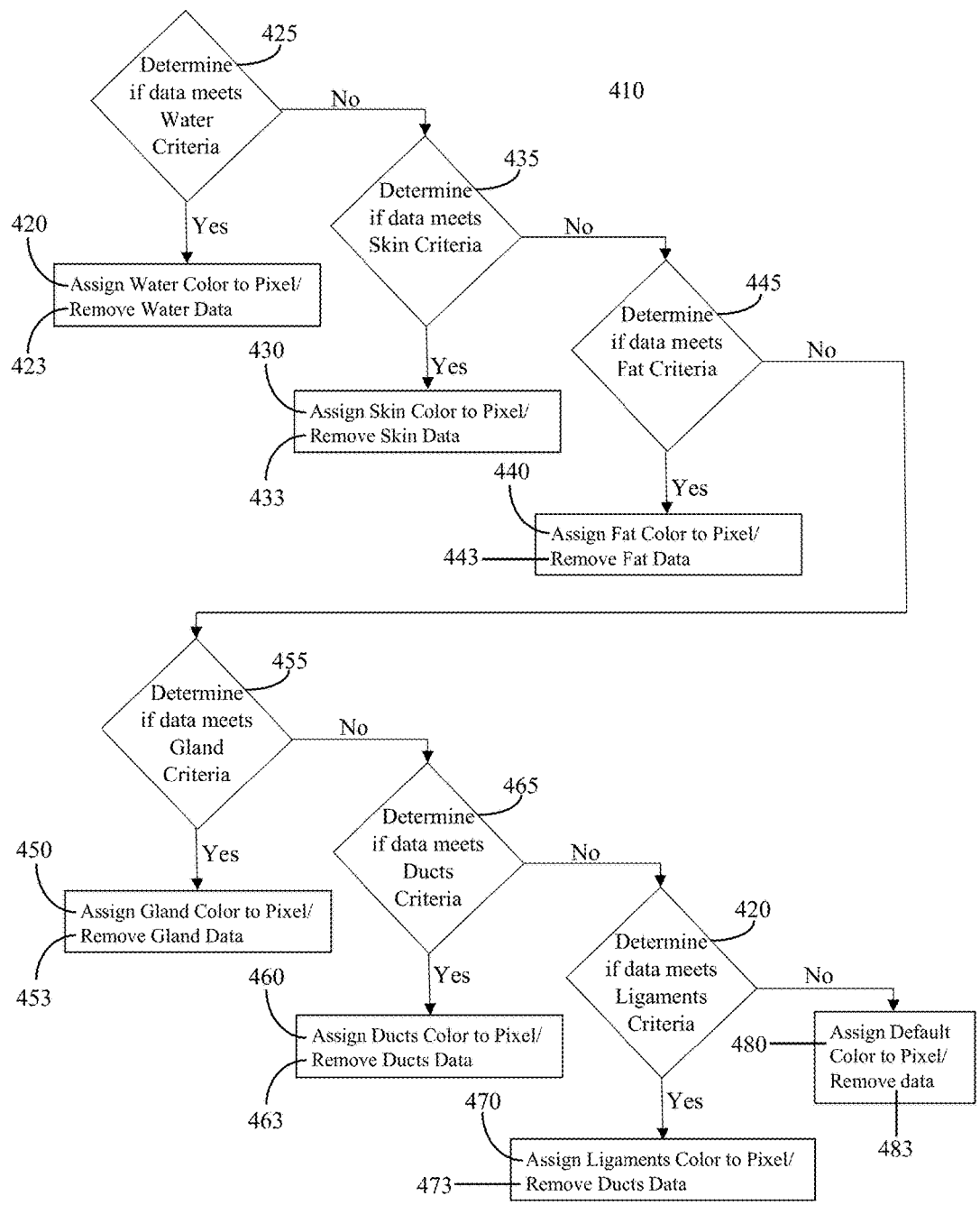
FIG. 4B illustrates one example implementation for tissue type identification using data from a QTUS system.

FIG. 4A illustrates a general process flow for tissue type identification; and FIG. 4B illustrates one example implementation for tissue type identification using data from a QTUS system. Referring to FIG. 4A, a tissue type identification process 400 can be carried out using speed of sound data 401, attenuation data 411, and reflection data 421 from, for example, a QTUS system. In some cases, this process may be carried out during the step of computing of speed of sound and attenuation images (360) and/or reflection images (370) as described with respect to FIG. 3. Data from the three images can be evaluated in combination pixel-by-pixel (or 'voxel'-by-'voxel') to determine tissue type for each pixel (405) and assign a pixel color (410). Tissue type identification (e.g., operation 405) may involve the application of any of the machine learning methods including, but not limited to, support vector machines, discriminant analyses, decision trees, and k-nearest neighbors', or a combination thereof.

Figure 5:
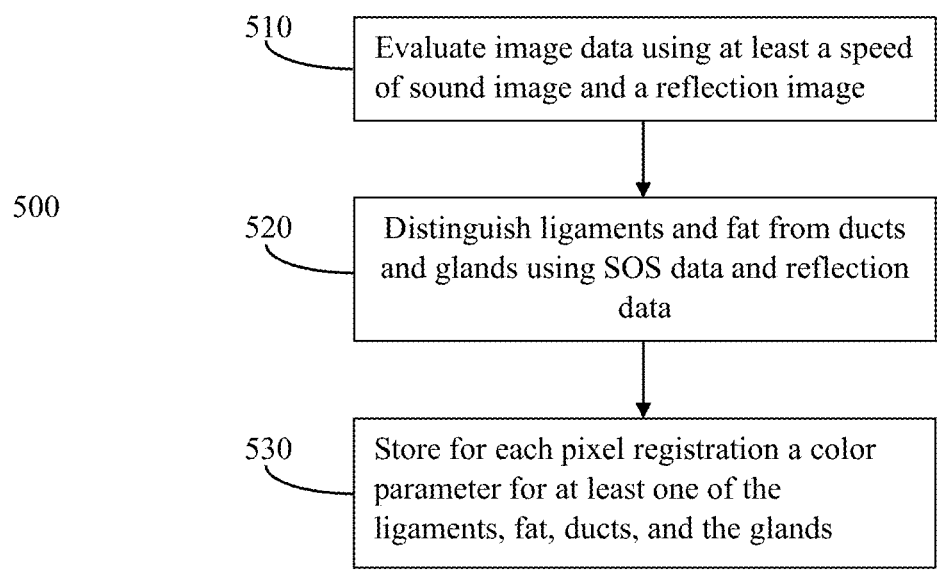
FIG. 5 illustrates a process flow for tissue type identification.

A pixel can be assigned a coloration (e.g., operation 410) based on the combined data for that pixel, and more particularly, based on the outcome of the determination process 405, which may be performed such as described with respect to FIG. 5. The coloration refers to data associated with color properties so that when the information from the QTUS system is transformed into an image, the color properties are reflected in the image. Color properties can be hue, intensity, and/or any other recognizable property of color. This color property can be used when generating a speed of sound image (or other image representing the ultrasound data) for display, and can be in any suitable format for rendering or otherwise displaying the image.

Referring to FIG. 4B, one example implementation of a process for assigning pixel color 410 can be a tree method for classifying the data and include performing a tissue identification process and color assignment in an order of classifying pixels into water/external, skin, fat, glands, ducts, and connective tissue. For example, the computer-executed method can include determining whether the data meets a water condition criteria (425). If the data does meet the condition criteria for likely being water, water coloration is assigned (420). In some implementations if the data does meet the condition criteria for likely being water, the data is removed from the image data (423).

The computer-executed method can further include determining whether the data meets a skin condition criteria (435). If the data does meet the condition criteria for likely being skin, coloration is assigned (430). In some implementations if the data does meet the condition criteria for likely being skin, the data is removed from the image data (433).

The computer-executed method can further include determining whether the data meets a fat condition criteria (445). If the data does meet the condition criteria for likely being fat, coloration is assigned (440). In some implementations if the data does meet the condition criteria for likely being fat, the data is removed from the image data (443).

The computer-executed method can further include determining whether the data meets a gland condition criteria (455). If the data does meet the condition criteria for likely being gland, coloration is assigned (450). In some implementations if the data does meet the condition criteria for likely being gland, the data is removed from the image data (453).

The computer-executed method can further include determining whether the data meets a duct condition criteria (465). If the data does meet the condition criteria for likely being duct, coloration is assigned (460). In some implementations if the data does meet the condition criteria for likely being duct, the data is removed from the image data (463).

The computer-executed method can further include determining whether the data meets a connective tissue condition criteria (475). If the data does meet the condition criteria for likely being connective tissue, coloration is assigned (470). In some implementations if the data does meet the condition criteria for likely being connective tissue, the data is removed from the image data (473).

If the data does not meet any of the condition criteria considered, a default coloration may be applied (480). In some implementations if the data does meet any of the condition criteria considered, the data is removed from the image data (483).

As mentioned above, a pixel can be assigned a coloration (e.g., operation 410) based on the combined data for that pixel, and more particularly, based on the outcome of the determination process 405, which may be performed such as described with respect to FIG. 5, which illustrates a process flow for tissue type identification. Referring now to process 500 of FIG. 5, the image data, including speed of sound and reflection images are evaluated to assign a color to each pixel registration (510). Each pixel of the speed of sound and reflection images are co-registered. Connective tissue and fat can be distinguished from ducts and glands using the speed of sound data and the reflection data (520). These and other tissue types can be distinguished (and classified) using statistical analysis (as explained in the discussion of FIGS. 7A-7C, 8, 9A-9B, and 10A-10B). For example, the connective tissue and the fat have speed of sound data less than that of ducts and glands, and the connective tissue have reflection data greater than the fat. Ducts and glands may be distinguished from each other using speed of sound data. Based on the tissue identification, each co-registered pixel is assigned a color parameter (530), the available color parameters being for the connective tissue, fat, ducts, glands, and other specified tissue types, and the color parameter is stored for each pixel. Storing the color parameter can include replacing at least the speed of sound data and reflection data of the pixel registration with the color parameter or adding the color parameter to at least the speed of sound data and the reflection data of the pixel registration.

Data from speed of sound, attenuation, and reflection images may all be used, individually and in any combination, to distinguish tissue types (ducts, fat, glands, and connective tissue) from one another. It should be noted that using speed of sound, attenuation, and reflection images in combination creates the most accurate modeling of each tissue type.

Figure 6A:
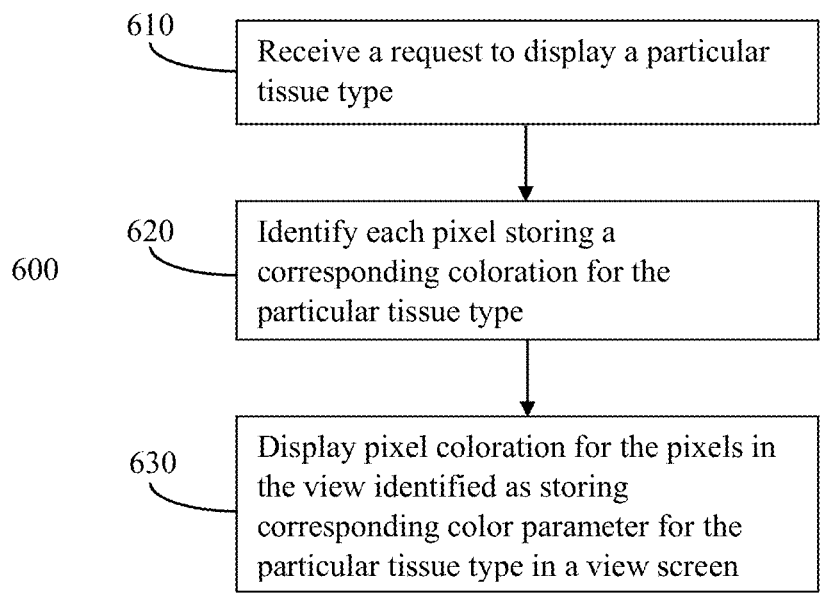
FIG. 6A illustrates a process flow for displaying a particular tissue type(s).
Figure 6B:
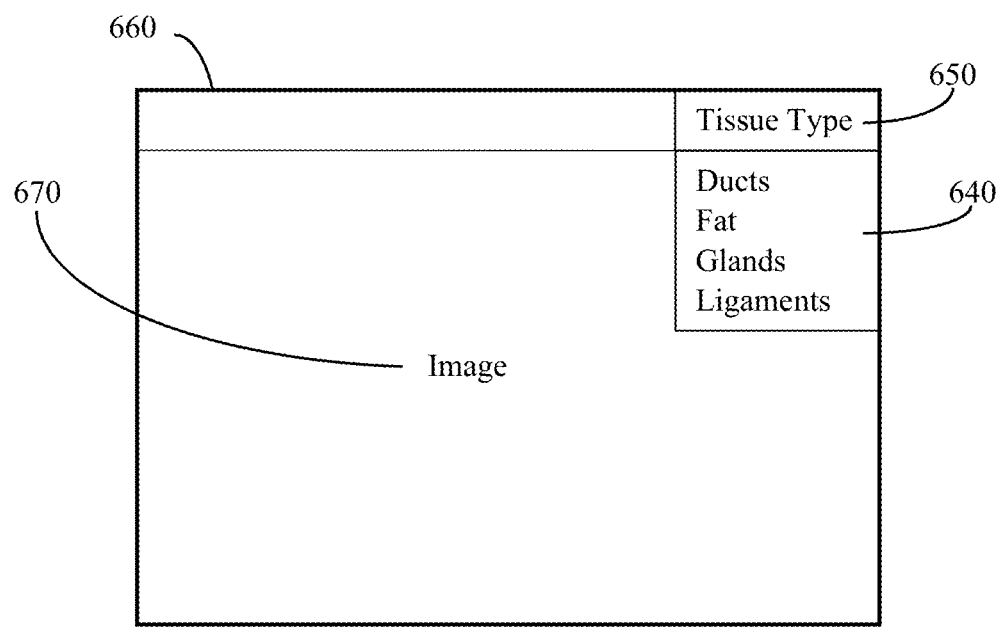
FIG. 6B is an example of a simplified graphical user interface for displaying identified tissue types.

FIGS. 6A and 6B illustrate using tissue type coloration. FIG. 6A illustrates a process flow for displaying a particular tissue type(s) and FIG. 6B is an example of a simplified graphical user interface for displaying identified tissue types. A process flow (600) incorporating the use of the described coloration to display tissue types is shown. A request to display a particular tissue type can be received (610), for example, via selection of a tissue type 640 in a dropdown menu 650 of a graphical user interface (GUI) 660. Once the request is received (610), each pixel that is storing the corresponding color to that particular tissue type is identified (620), and the appropriate pixels in the view screen 670 of the GUI 660 can be displayed with corresponding coloration for the selected particular tissue type (630). The GUI of FIG. 6B is an example of a simplified graphical user interface for displaying identified tissue types; and through which a user can select which tissue type(s) the user would like to be highlighted in the display image.

Figure 6C:
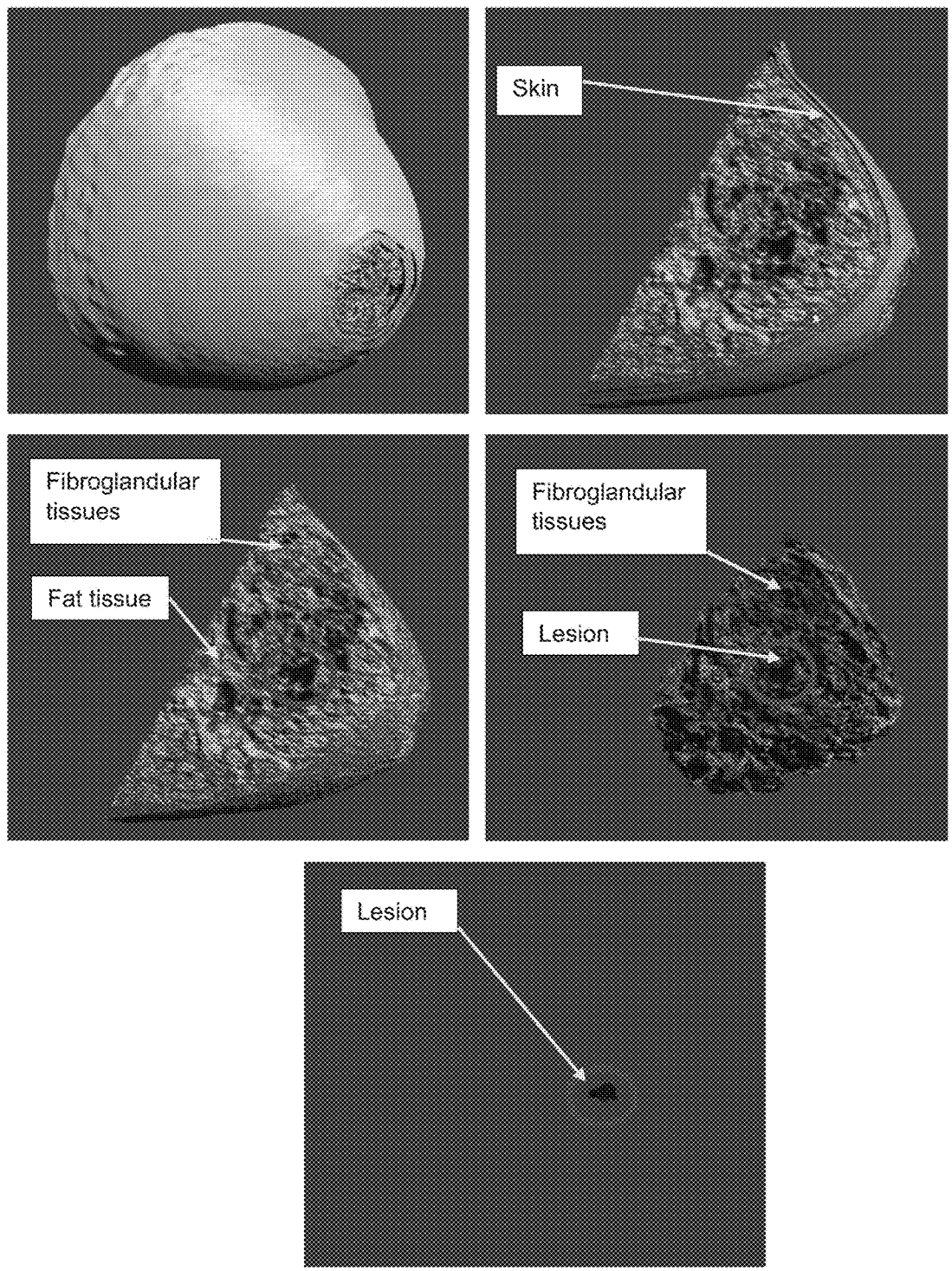
FIG. 6C shows a set of example images where particular tissue or tissues are isolated.

FIG. 6C shows a set of example images where particular tissue or tissues are isolated. Referring to FIG. 6C, a graphical user interface can display an image where a particular tissue or tissues isolated based on type or color for better visualization of their shape, size and location. In some cases, the system can display an isolated tissue or tissues based on a selected tissue type or color. The selection of tissue type and/or color may be made via suitable user interface commands. In FIG. 6C, a set of images showing isolation of a lesion from skin, fibroglandular tissues, and fat tissue can be seen in progression via the color coded images.

FIGS. 7A-7C, 8, 9A-9B, and 10A-10B illustrate processes of distinguishing tissue types by using statistical analysis of the data from speed of sound, reflection, and attenuation images.

Figure 7A:
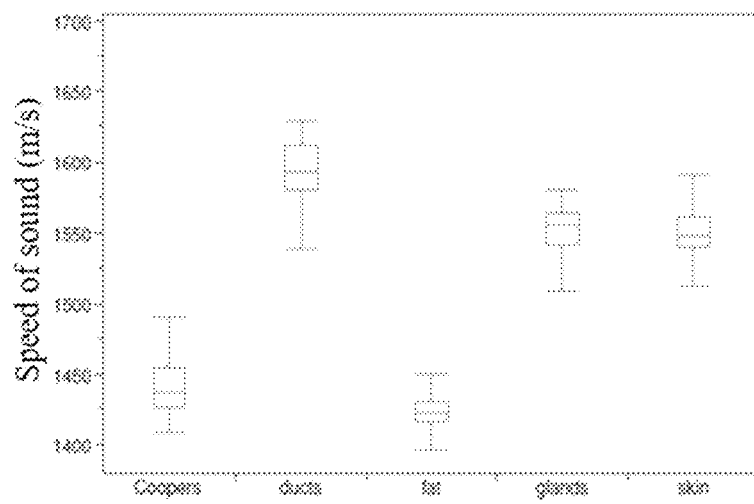
FIGS. 7A-7C show speed of sound, attenuation and reflection characteristics, respectively, as a function of breast tissue type for a feasibility study.
Figure 7B:
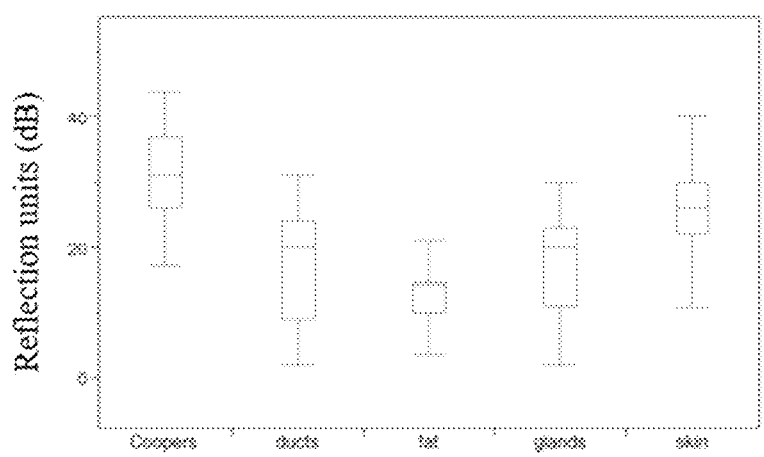
Figure 7C:
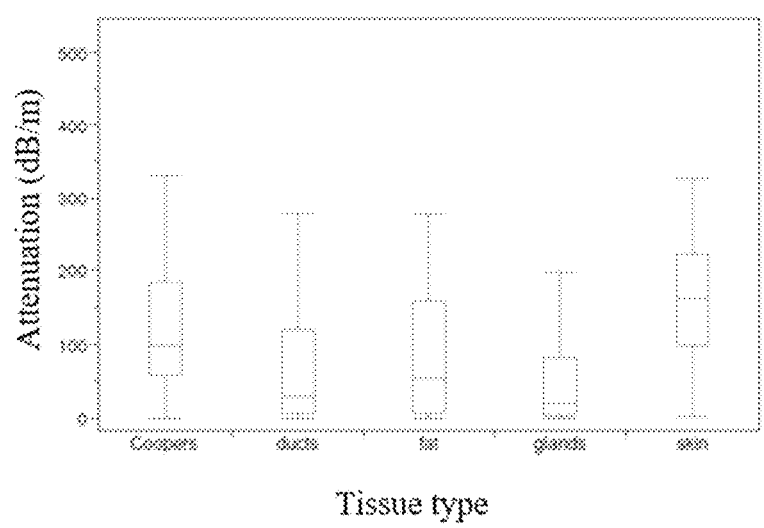

FIGS. 7A-7C show speed of sound, attenuation, and reflection characteristics, respectively, as a function of breast tissue type for a feasibility study. This data was collected using QTUS methods (described in more detail in the Example section). The data in FIGS. 7A-7C are displayed in the form of box plots, with the center bar of each box representing the median value of that measurement, the upper and lower bounds of the box representing the 75% quantile and 25% quantile values, and the upper and lower ends of the whiskers denoting the maximum and minimum values excluding the outliers.

As can be seen by looking at FIG. 7A, the speed of sound graph provides the most distinct variation between data collected for the tissue types. Fat has the slowest speed of sound and shares some overlap with connective tissue such as Cooper's ligaments. Glands and skin come next, with ducts having the fastest speed of sound. It should be noted that while some overlap in speed of sound measurements for tissue types is found, for most patients, it can be possible to identify separation in values of speed of sound for tissue types, from slowest to fastest, in the order of fat, connective tissue, skin, glands, and ducts. Shape-based and spatial-based recognition techniques can be used to further distinguish between tissue types in addition to using the SOS, reflection, and attenuation data.

As can be seen by looking at FIG. 7B, the reflection graph shows further distinctions between tissue types. In general, fat has the lowest reflection measurement, followed by ducts and glands (each being approximately equal to one another), skin, and finally Cooper's ligaments in that order from lowest to highest is found. It should be noted that while fat and Cooper's ligaments share significant overlap in the speed of sound graph shown in FIG. 7A, in the reflection units graph of FIG. 7B, fat and connective tissue share minimal overlap. Therefore, data from these two measurement types (speed of sound and reflection) can be used in combination to differentiate the various tissue types (as mentioned with respect to FIG. 5).

As can be seen by looking at FIG. 7C, the attenuation graph provides additional measurements that can be used to distinguish tissue types. Generally, glands have the lowest attenuation measurements, followed by ducts, fat, connective tissue and skin. While there is a significant overlap in the tissue types attenuation data, these measurements can be used in combination with SOS and reflection data to increase the probability that the tissue types are identified correctly.

FIG. 8 shows a table of the results of a non-parametric Mann-Whitney U Test. Here, the statistical comparison between each pair of tissue types for SOS, reflection, and attenuation data are provided. The p-values for each pair of tissue types were obtained using the non-parametric Mann-Whitney U-Test for all pairs of tissue types. It should be noted that using this test, a p-value of less than 0.05 indicates significance. Thus, it can be seen that in the reflection data, only glands and ducts do not show significant differences in measured data and that in the SOS data only skin and glands do not show significant differences in measured data. This means that when the non-parametric Mann-Whitney U-Test is applied to SOS data and reflection data, and then the results are combined, criteria for the confirmation of tissue types is satisfied across all pairs of tissue types. Furthermore, Holm correction was applied to control the probability of false positive error accumulated in a sequence of multiple comparisons.

It should be noted that the graphs of FIGS. 7A-7C were made from data taken from a number of patients. Individual results may vary, such as a patient with a slower speed of sound measurement in connective tissue than fat. However, when combining measured data from each of the speed of sound image, reflection image, and attenuation image for an individual patient and implementing machine learning, the identification of tissue types can be performed with higher confidence.

Figure 9B:
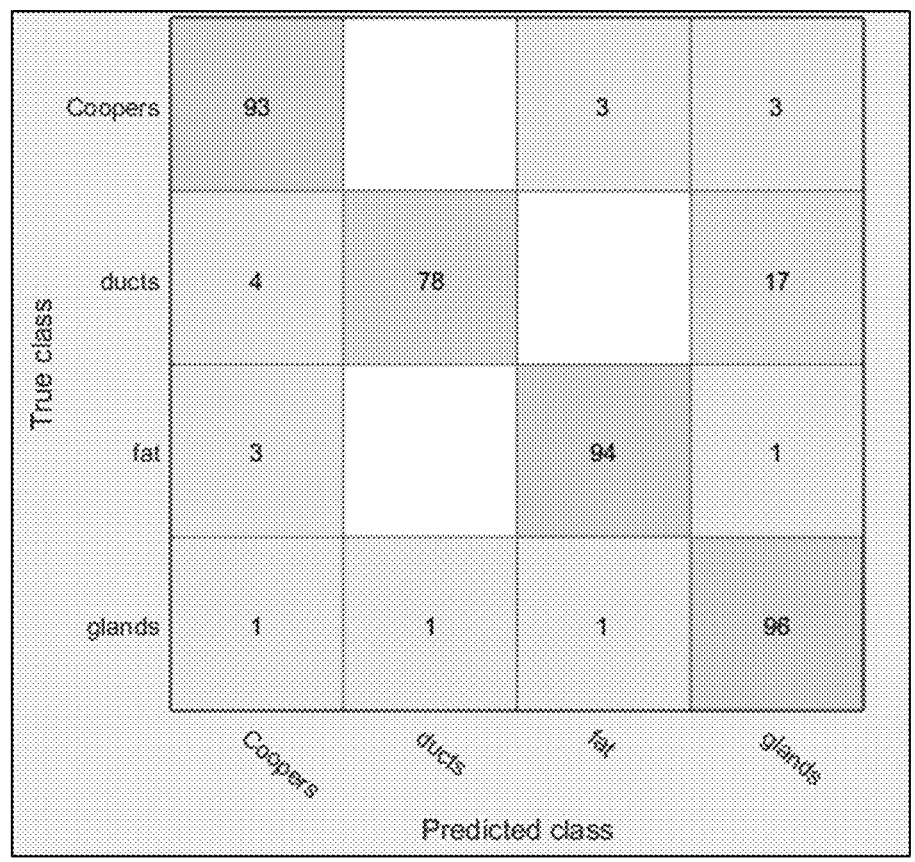
FIG. 9B shows a confusion matrix for four tissue types.

FIGS. 9A and 9B illustrate confusion matrices for five and four tissue types, respectively. FIG. 9A provides a classification performance table assessed by 50-fold cross validation on five tissue types. FIG. 9B provides a classification performance table assessed by 50-fold cross validation on four tissue types. Although radial basis function support vector machines utilizing a Gaussian kernel were used in the illustrated examples, it should be noted that other classification strategies may also be used, such as (but not limited to) linear support vector machines, discriminant analyses and neural networks. In FIG. 9A, skin is included as a tissue type for classification, however, FIG. 9B illustrates the case with the skin data points removed from the overall data.

As can be seen in FIG. 9B, the only predicted tissue type that is not at least 93% accurate is predicted ducts. The reason for this is believed to be attributable to predicted glands that are actually ducts, accounting for 17% of the inaccuracy. However, by using shape-based geometric information, as explained below, the accuracy for predicting ducts can be greatly improved.

As shown in FIG. 7A, skin shares some similar values to other tissue types, such as similar to glands in the speed of sound graph. This can make differentiation between the skin and other tissue types challenging, therefore, it is advantageous to use other methods to distinguish skin from other tissue types. Any suitable method can be used to remove pixels associated with skin from the image. One such method is performed by spatially identifying the surface of the breast in relation to the surrounding fluid. The surrounding fluid will have a distinct attenuation measurement (with water having essentially zero attenuation). The breast tissue is then encountered and everything from that point towards the center of the breast is considered breast tissue. Pixels that are ascertained to be close to the border between breast tissue and water are marked as border pixels. The attenuation image data is then fused with the speed of sound (for skin) data. As can be seen in FIG. 7A, skin and gland tissue both have relatively high speed of sound than that of fat and can be segmented based on this information. Finally, the skin is removed from the gland tissue by noting the proximity of the pixel to the border between breast tissue and water. After the skin data is removed, the predicted tissue types of glands and ducts are greatly increased as can be seen in the difference between FIGS. 9A and 9B (glands +19% accuracy and ducts +6% accuracy).

In some implementations, the accuracy of predicting tissue types within the breast can be improved by employing shape-recognition based geometric information. For instance, assuming ducts are relatively continuous and 'connected' across axially adjacent images, misclassification of ducts as glands can be improved. This form of geometric information may also be embedded in second order statistics, such as gray level co-occurrence matrices. By employing shape-recognition based geometric information, the accuracy of predicting ducts can be greatly improved from the 77% prediction accuracy shown in FIG. 9B, while the misclassification of actual ducts as predicted glands (17%) can be greatly reduced.

Figure 10A:
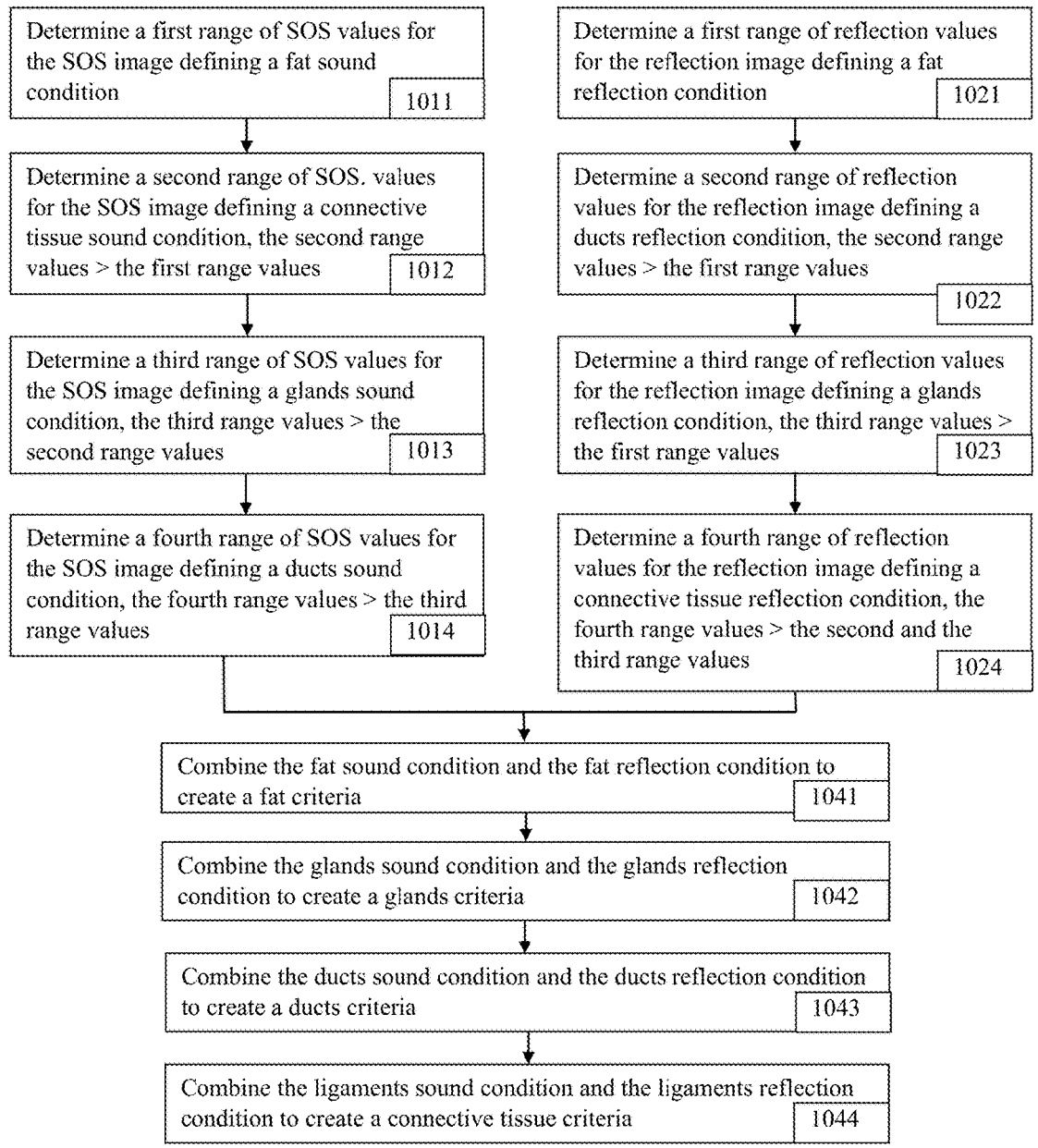
FIG. 10A illustrates a method of combining speed of sound data with reflection data to create tissue type criteria.
Figure 10B:
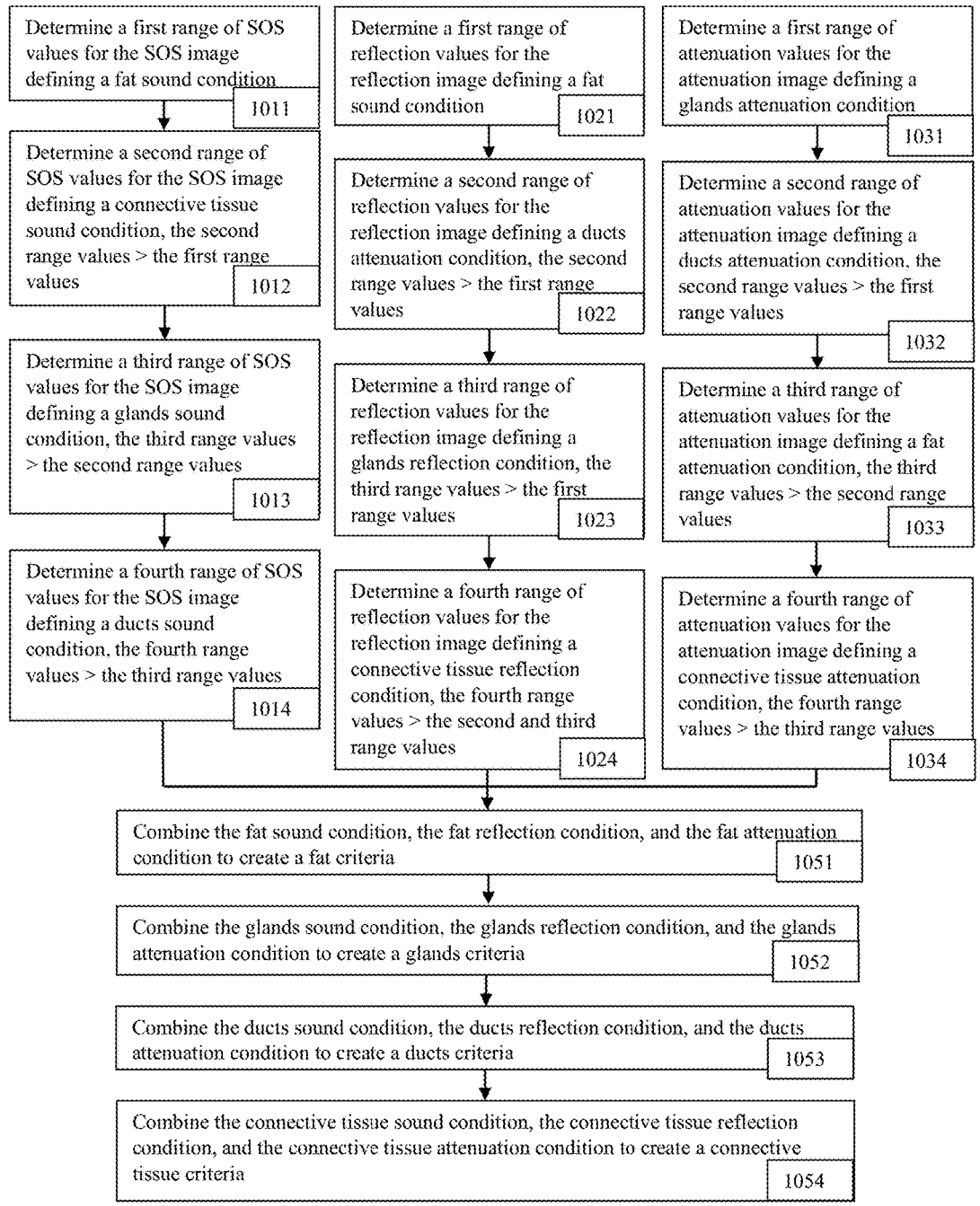
FIG. 10B illustrates a method of combining speed of sound data, reflection data, and attenuation data to create tissue type criteria.

FIG. 10A illustrates a method of combining speed of sound data with reflection data to create tissue type criteria; and FIG. 10B illustrates a method of combining speed of sound data, reflection data, and attenuation data to create tissue type criteria.

Understanding that for a certain individual, the speed of sound data for fat may be higher or lower than the median is an important aspect to predicting tissue types and why, in this embodiment, pre-determined ranges are not implemented. As measured by the speed of sound and as shown in FIG. 7A, fat generally has the lowest SOS values, followed by connective tissue, glands, and ducts having ascending SOS values in that order. With this in mind, after data has been collected for SOS values using QTUS methods for SOS, a first range of SOS values for the SOS image defining a fat sound condition can be determined (1011), for example, via a hardware processor executing software; and a second range of SOS values for the SOS image defining a connective tissue sound condition can be determined, where the second range has higher values than the first range (1012). A third range of SOS values for the SOS image defining a glands sound condition can be determined, where the third range has higher values than the second range (1013); and a fourth range of SOS values for the SOS image defining a ducts sound condition can be determined, where the fourth range has higher values than the third range (1014). The ranges may be identified by sorting pixel values from lowest speeds to highest speeds and finding the breaks in the speeds by which to define each condition. In some cases, machine learning algorithms or other iterative algorithms may be used to identify boundary conditions.

In general, as illustrated in the reflection graph of FIG. 7B, fat has the lowest reflection values, followed by ducts and glands (ducts and glands being approximately equal), and connective tissue in ascending order. Accordingly, after data has been collected for reflection values using QTUS methods for reflection, a first range of reflection values for the reflection image defining a fat reflection condition can be determined (1021), for example via the hardware processor executing software; and a second range of reflection values for the reflection image defining a ducts reflection condition (1022) and a third range of reflection values for the reflection image defining a glands reflection condition (1023) can be determined, the second and third ranges can have higher values than the first range. A fourth range of reflection values for the reflection image defining a connective tissue reflection condition can be determined, where the fourth range has higher values than the second and third ranges (1024). The ranges may be identified by sorting pixel values from lowest values to highest values and finding the breaks in the speeds by which to define each condition. In some cases, machine learning algorithms or other iterative algorithms may be used to identify boundary conditions. In some cases, speed of sound data determinations can be used to support a classification of pixel, and a corresponding reflection value categorization.

The fat sound condition and the fat reflection condition can be combined to create a fat criteria (1041), the glands sound condition and the glands reflection condition can be combined to create a glands criteria (1042), the ducts sound condition and the ducts reflection condition can be combined to create a ducts criteria (1043), and the connective tissue sound condition and the connective tissue reflection condition can be combined to create a connective tissue criteria (1044).

In another implementation as shown in FIG. 10B, attenuation values are incorporated in the process to create the ducts, fat, glands, and connective tissue criteria. As shown in FIG. 7C, for attenuation, glands generally have the lowest attenuation values, followed by ducts, fat and connective tissue in ascending order. The process with respect to SOS values and reflection values can be the same as those described above in FIG. 10A. However, for the process illustrated in FIG. 10B, the processor executing software can determine a first range of attenuation values for the attenuation image defining a glands attenuation condition (1031). In addition, a second range of attenuation values for the attenuation image defining a ducts attenuation condition can be determined, where the second range has higher values than the first range (1032). A third range of attenuation values for the attenuation image defining a fat attenuation condition can be determined, where the third range has higher values than the second range (1033). In addition, a fourth range of attenuation values for the attenuation image defining a connective tissue attenuation condition can be determined, where the fourth range has higher values than the third range (1034). As with the SOS and reflection data values, the ranges for the attenuation conditions may be identified by sorting pixel values from lowest values to highest values and finding the breaks in the speeds by which to define each condition. In some cases, machine learning algorithms or other iterative algorithms may be used to identify boundary conditions. In some cases, speed of sound data determinations (and/or reflection data determinations) can be used to support a classification of pixel, and a corresponding attenuation value categorization.

In the implementation shown in FIG. 10B, the fat sound condition, the fat reflection condition, and the fat attenuation condition can be combined to create a fat criteria (1051); the glands sound condition, the glands reflection condition, and the glands attenuation condition can be combined to create a glands criteria (1052); the ducts sound condition, the ducts reflection condition, and the ducts attenuation condition can be combined to create a ducts criteria (1054); and the connective tissue sound condition, the connective tissue reflection condition, and the connective tissue attenuation condition can be combined to create a Cooper's ligaments criteria (1054).

Figure 11A:
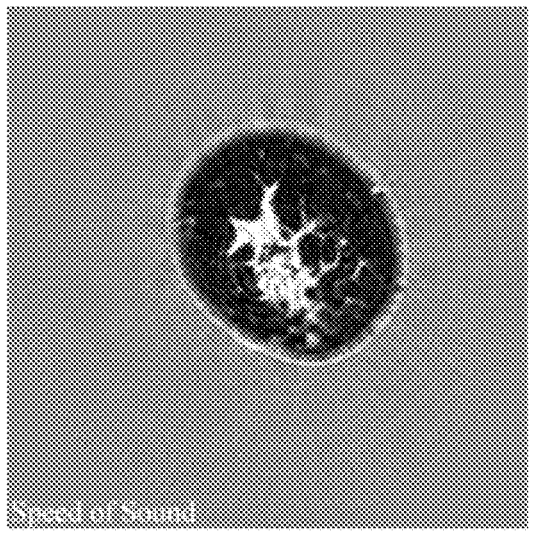
FIG. 11A-11D show speed of sound, attenuation, reflection and colored images, respectively, from a QTUS image of a patient's breast classified using an SVM classifier.
Figure 11B:
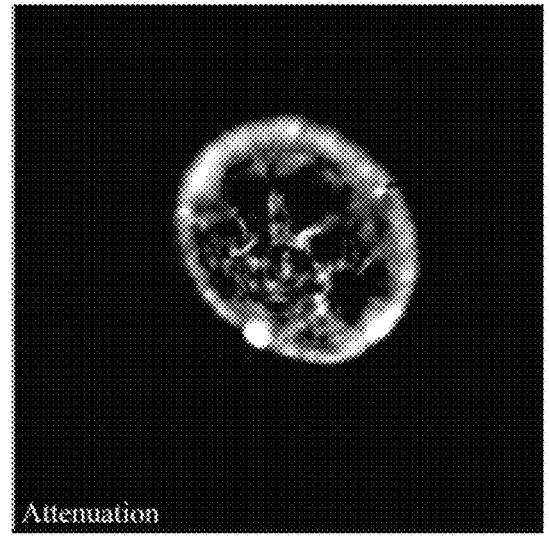
Figure 11C:
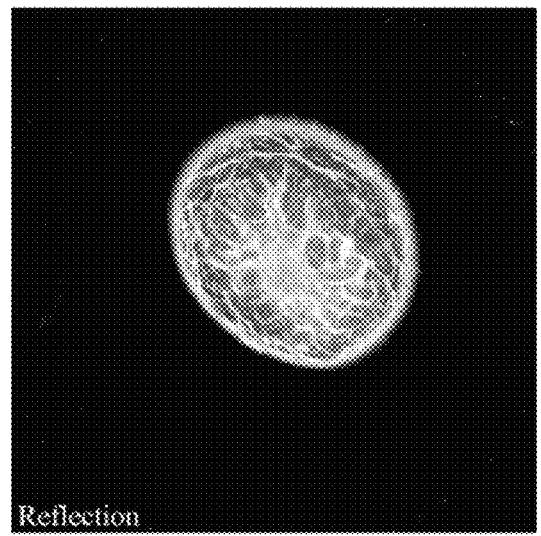
Figure 11D:
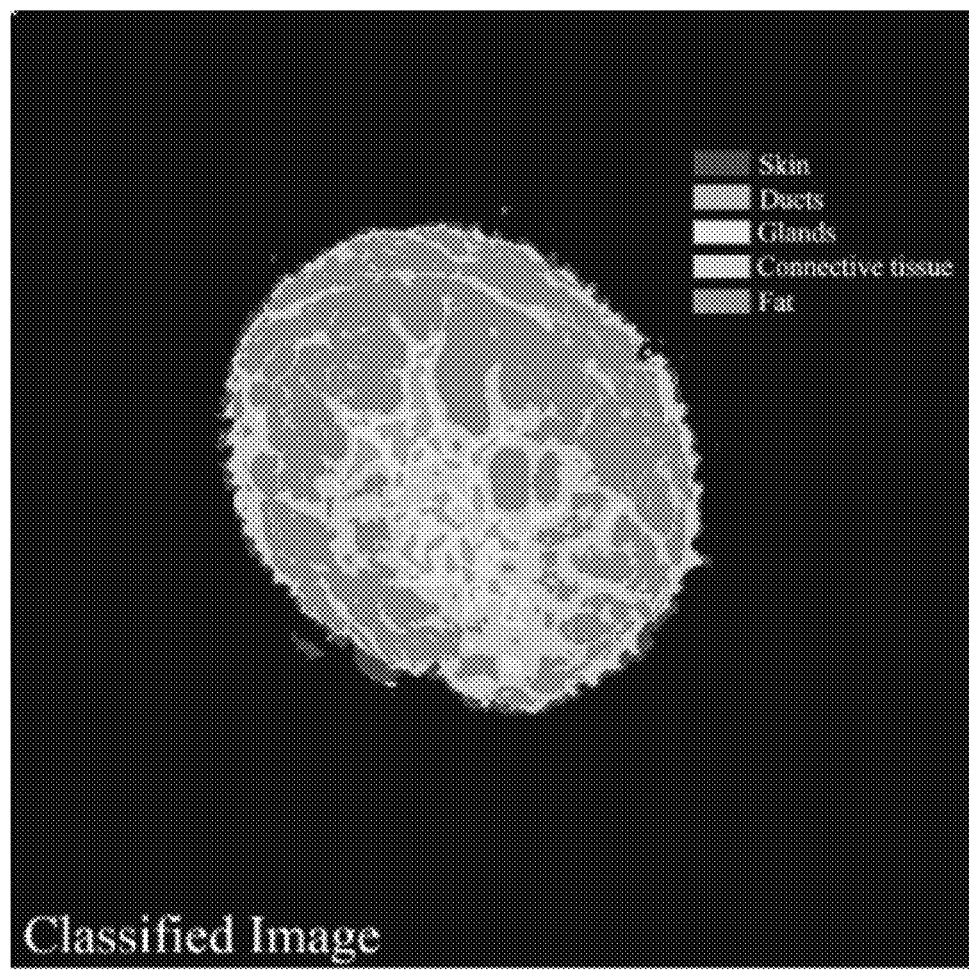

FIG. 11A shows a speed of sound image of a normal breast, FIG. 11B shows an attenuation image of the normal breast and FIG. 11C shows a reflection image of the normal breast. Using the described techniques, the tissue types can be classified and colored. As can be seen in the classified image of FIG. 11D, coloration has been assigned to several tissue types. There may be a spectrum of colors assigned to the skin, fat, gland, duct, and Cooper's ligament tissue types and/or a same color but different intensity may be used. In a specific implementation shown in the color image, tissue types are color coded: ducts are orange, glands are yellow, fat is blue, Cooper's ligaments (connective tissue) are green, and skin is red. In other implementations, skin is removed from the image because the skin may not be considered important by a clinician since the skin can be examined visually.

Process flow 300 described with respect to FIG. 3, process flow 400 described with respect to FIG. 4A, process flow 500 described with respect to FIG. 5, and process flow 600 described with respect to FIG. 6 may be implemented in the form of computer-executable instructions, such as program modules, that are executed by one or more computers or other devices.

In some embodiments, the machine/computer system can operate as a standalone device. In some embodiments, the machine/computer system may be connected (e.g., using a network) to other machines. In certain of such embodiments, the machine/computer system may operate in the capacity of a server or a client user machine in server-client user network environment, or as a peer machine in a peer-to-peer (or distributed) network environment.

The machine/computer system can be implemented as a desktop computer, a laptop computer, a tablet, a phone, a server, or any other machine capable of executing a set of instructions (sequential or otherwise) that specify actions to be taken by that machine, as well as multiple machines that individually or jointly execute a set (or multiple sets) of instructions to perform any one or more of the methods described herein.

The computer system can have hardware including one or more central processing units (CPUs) and/or digital signal processors (DSPs), memory, mass storage (e.g., hard drive, solid state drive), I/O devices (e.g., network interface, user input devices), and a display (e.g., touch screen, flat panel, liquid crystal display, solid state display). Elements of the computer system hardware can communicate with each other via a bus.

Figure 12:
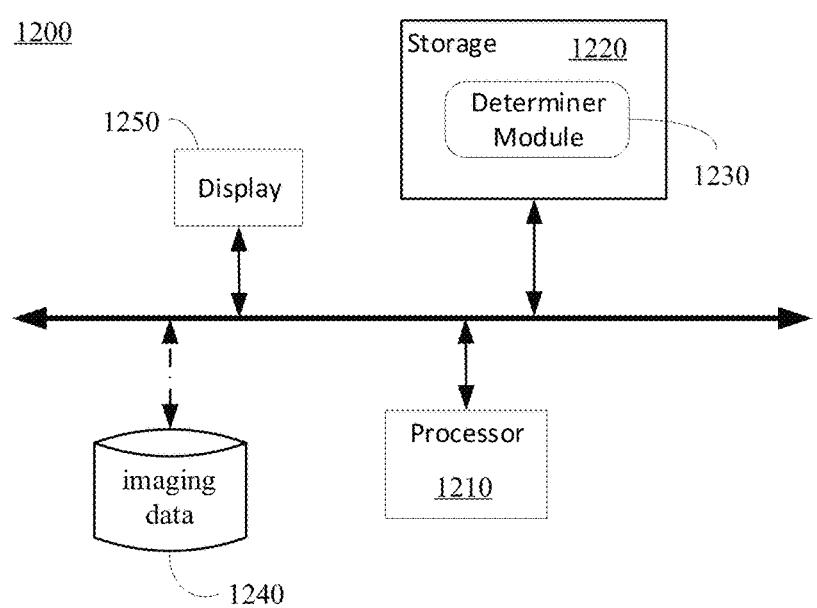
FIG. 12 shows an example computing system through which tissue type identification may be carried out.

For example, FIG. 12 shows an example computing system through which tissue type identification, including detection and determination, may be carried out. In some implementations, the computing system may be embodied, at least in part, as a viewing station and/or PACS. In some implementations, the computing systems may embody, at least in part, the acquisition control system. Referring to FIG. 12, the system 1200 can include a processor 1210 and a storage system 1220 in which a tissue type determiner module 1230 may be stored. The tissue type determiner module may carry out process 400 such as described with respect to FIGS. 4A-4B and process 500 such as described with respect to FIG. 5. Examples of processor 1210 include general purpose central processing units, application specific processors, and logic devices, as well as any other type of processing device, combinations, or variations thereof. The processor 1210 processes data according to instructions of the tissue type determiner module 1230.

Storage system 1220 includes any computer readable storage media readable by the processing system 1220 and capable of storing software, including tissue type determiner module 1230. Storage system 1220 may include volatile and nonvolatile, removable and non-removable media implemented in any method or technology for storage of information, such as computer readable instructions, data structures, program modules, or other data. Examples of storage media include random access memory (RAM), read only memory (ROM), magnetic disks, optical disks, CDs, DVDs, flash memory, solid state memory, phase change memory, or any other suitable storage media. Certain implementations may involve either or both virtual memory and non-virtual memory. In no case do storage media consist of a propagated signal or carrier wave. In addition to storage media, in some implementations, storage system 1220 may also include communication media over which software may be communicated internally or externally.

Storage system 1220 may be implemented as a single storage device but may also be implemented across multiple storage devices or sub-systems co-located or distributed relative to each other. Storage system 1220 may include additional elements, such as a controller, capable of communicating with processor 1210.

A database 1240 storing speed of sound, reflection, and other imaging data from a QTUS system can be coupled to the system via wired or wireless connections.

Visual output can be provided via a display 1250. Input/Output (I/O) devices (not shown) such as a keyboard, mouse, network card or other I/O device may also be included. It should be understood the any computing device implementing the described system may have additional features or functionality and is not limited to the configurations described herein.

The determiner module 1230, for example, in the case of one implementation of process 1200, can take advantage of the correlation of the image data to anatomy and pathology for identifying tissue types in breast tissue. For example, as part of, or associated with, a thresholding step.

Figure 13A:
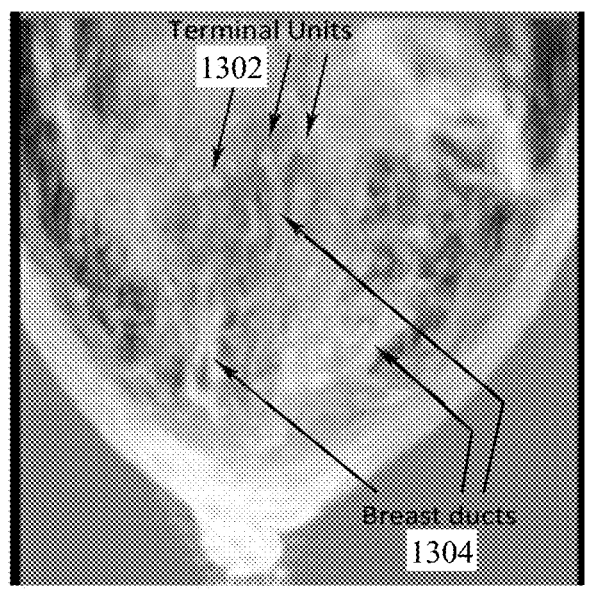
FIG. 13A shows a QTUS transmission image of a normal breast.
Figure 13B:
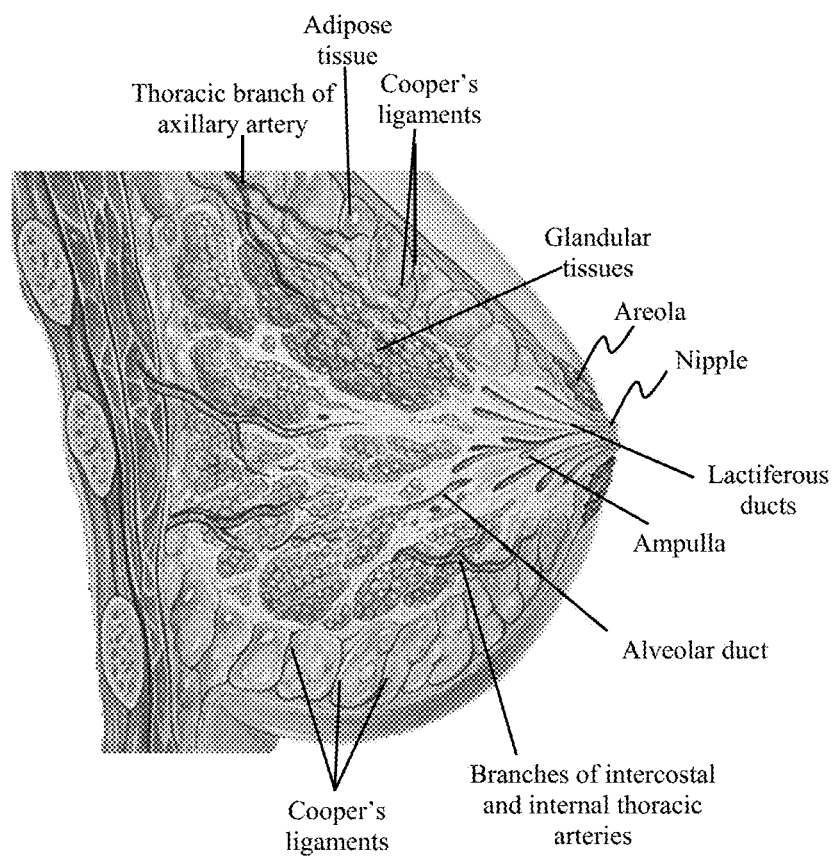
FIG. 13B identifies breast anatomy from a Patrick Lynch rendering of breast anatomy

FIG. 13A shows a QTUS transmission image of a normal breast; and FIG. 13B identifies breast anatomy from a Patrick Lynch rendering of breast anatomy. Comparing the two images, it can be seen that the QTUS transmission image of a normal breast demonstrates the ductal 1302 and terminal duct 1304 lobular units in the axial plane; and shows good anatomic correlation with the artist's rendering of breast anatomy in FIG. 13B.

Example—Feasibility Study; Statistical Analysis

Volunteer Preparation and Imaging:
An adhesive pad with a magnet was placed near the nipple region of the breast. The breast was immersed in a water tank and positioned such that the magnet attached to the nipple is docked to a magnetized retention rod that gently holds the breast in a consistent position during the scan.

Ultrasound Imaging:
The volunteers were scanned on QT Ultrasound prototype scanners, Briefly, in transmission mode, the transmitter emits a plane wave which traverses the breast tissue and is received by the receiver on the opposite end. In this case, the receiver was a 1536 element PZT array with data acquisition rate of 33.3 Ms/s at 14-bits per sample. Multiple acquisitions at frequencies ranging from 0.3 to 1.5 MHz were acquired for 180 angles as the transmitter-receiver combination is rotated around the subject. The acquired projection information was used for image reconstruction using nonlinear inverse scattering in 3D. The result of this reconstruction is a three-dimensional map of complex refractive index values, consequently providing image volumes of both of speed of sound and attenuation. In reflection mode, there are three reflection transducers (4 MHz center frequency) with different focal lengths to extend the overall depth of focus within the imaging volume. The acquired images were spatially compounded and corrected for refraction using the corresponding speed of sound information. The spatial compounding results in significant reduction of image speckle while maintaining the high resolution nature of the images similar to that of traditional B-mode ultrasound. The end result of each scan is a 3D volume of essentially three different modalities: speed of sound, attenuation, and reflection. Note that the transmission and reflection data acquisition is time multiplexed, and after calibration, the respective image stacks are perfectly co-registered.

Statistical Analysis:
In order to build (train and validate) a classifier, 99 regions of interest (ROI) for each breast tissue type were identified across thirteen breast studies. The breast tissue types are: ducts, glands, fat, skin and Cooper's ligaments. Each ROI is essentially a single voxel with dimensions of 400 μm×400 μm×1 mm. The number of ROIs per study varied from 6 to 8, in order to account for inter-subject variability, if any. The ability of the three QTUS image features to distinguish between breast tissue types was first assessed. The nonparametric Mann-Whitney U-test was performed between every pair of classes, wherein $p<0.05$ was considered significant. Holm correction was applied to control the probability of false positive error accumulated in a sequence of multiple comparisons. Any features which showed insignificant differences were not included in further analysis. The features set was then used as feature vector in Support Vector Machines (SVM) algorithm for statistical classification. Both linear and nonlinear SVM classifiers were tested. Specifically, the nonlinear SVM approach was tested with Gaussian kernel function. In both instances, a 50-fold cross-validation was adopted in order to assess the classification performance. The algorithm was then validated on whole breast volumes to demonstrate the clinical application of the classifier.

Image Segmentation:
The QTUS images were acquired with breast inside a water tank. Therefore, the image space consists of both breast tissue and the surrounding water. Before going forward with image classification, the water surrounding the tissue within the images was removed using an algorithm originally developed to estimate breast density in the sense of BI-RADS, which uses the attenuation images wherein the skin is clearly identified as a relatively high attenuation structure within the surrounding water with essentially zero attenuation. For any given slice, the algorithm starts from the edge of the image (water) and move pixel-by-pixel inwards (towards breast tissue). Once the breast surface is encountered, everything from that point until the center of the breast is considered breast tissue (convexity assumption). Pixels that are ascertained to be close to the border between breast tissue and water are marked as border pixels. This information provided by the attenuation image is then fused and used along with speed of sound (for skin) to segment the speed of sound image. This is appropriate since both the images are co-registered. As noted below in results, the skin and fibroglandular tissue both have relatively high speed of sound than that of fat and are segmented out based on that. The last step is that skin is now removed from the fibroglandular tissue by noting the proximity of the pixel to the border between breast tissue and water as determined by the attenuation based segmentation.

Implementation:
The technical methods and approaches described above were implemented using MATLAB (R2016a, Mathworks, Natick, Mass.) and ImageJ (National Institutes of Health, Bethesda, Md.) software on a standard computer workstation (Intel Core i7 3.6 GHz, 16 GB RAM). Both custom written routines and built-in application and functions were used in MATLAB towards overall implementation of the methods.

Figure 14:
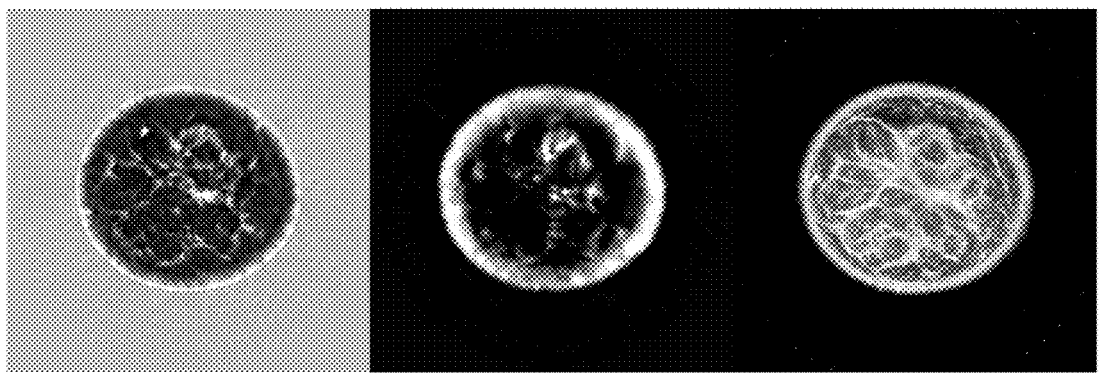
FIG. 14 shows speed of sound, attenuation and reflection QTUS images of a healthy breast.

Results:

QTUS characteristics of breast tissue: As mentioned above, a single QTUS whole breast scan and data processing generates three co-registered volumes corresponding to speed of sound, attenuation and reflection characteristics of the tissue. A representative image set is shown in FIG. 14. Speed of sound, attenuation, and reflection images are shown from left to right.

The data summary statistics for all the ROIs across thirteen studies are provided in FIGS. 7A-7C discussed above. Note that the center bar of each box in the box-plots represents the median value of that variable. The upper and lower bounds of the box mark the 75% quantile and 25% quantile values, and the upper and lower ends of the whiskers denote the maximum and minimum values excluding the outliers, respectively. The speed of sound range values associated with difference tissue types provided most distinct values and also proved to be the most significant contributor to the classifier. In general, ducts show the highest speed of sound out of all normal tissue types followed closely by glands and skin, in that order. Fat shows the lowest speed of sounds, typically under 1450 m/s. Cooper's ligaments appear as high reflection structures with relatively low speed values. Skin and Cooper's ligaments exhibit high reflection which is similar to that as seen in conventional B-mode ultrasound. The attenuation values show least amount of distinction as a function of tissue types.

Statistical Analysis and classification: The statistical comparison between each pair of tissue types for the three modalities is shown in the table of FIG. 8. It is worth noting that the comparisons associated with speed of sound and reflection show significant differences for all but one comparison—skin and glands for speed of sound, and glands and ducts for reflection. For every tissue type comparison there is at least one out of three modalities which shows a significant difference, demonstrating the complementary nature of the QTUS image features.

Two classification strategies are used in this example, (1) linear Support Vector Machines (SVM), and (2) radial basis function SVM which utilizes a Gaussian kernel. While both methods provided over 80% accuracy in classification, Gaussian SVM provided slightly higher accuracy rate of 85.2% in comparison to linear SVM which show provided accuracy of 83.2%. FIG. 9A shows the confusion matrix associated to this 5-class Gaussian SVM classifier.

As mentioned above, attenuation images may be used to classify and segment skin in a breast-specific manner, utilizing the anatomy of the breast tissue. By doing so, a 4-class problem remains. The classifier performance now improved significantly to 91.4% demonstrating the strength of the QTUS image features in demarcating normal breast tissue types. The modified confusion matrix is shown in FIG. 9B.

Image volume segmentation: The SVM classifier developed above was then used to classify whole breast image volumes. A representative example of this classification is shown in FIGS. 11A-11D. The resulting image in FIG. 11D has been color coded as a function of breast tissue types. Such a visual model can be instructive in evaluation of breast pathologies and also serve as a tool to guide further CAD development.

Discussion:

In all instances, QTUS scanning provided seamlessly co-registered volumetric speed of sound, attenuation and reflection images. As noted in multiple comparisons of FIG. 8, each of these modalities provide mostly significant differences in comparison of tissue types. Speed of sound is clearly an important contributor towards the classification. A sequential floating forward selection (SFFS) method was used in order to establish the order of feature importance. The result, in order of importance, was: speed of sound, reflection, and attenuation. It is of note, as applicable in any ultrasound system, the reflection data is not quantitative. It is a sensitive function of several factors including complexity of the scatterers' shape, local angle of incidence of the beam, and the attenuation of the intervening medium. Nevertheless, when comparing the range of reflection values over many case studies, as done in this example, the range of reflection values associated with different tissue types was still relatively distinct enough to serve as an important feature in image classification.

Both speed of sound and attenuation maps are derived from the complex refractive index of the tissue medium, wherein the two modalities are associated with the real and imaginary parts of the refractive index, respectively. Together with the reflection map, which is essentially a spatially compounded, extended depth-of focus version of conventional B-mode ultrasound (with refraction correction), the three modalities provide highly complementary and synergistic information for most breast tissue types.

While this example uses a non-linear SVM classifier, the strength of the data provided by QTUS images is such that most of the frequently used classifiers in machine learning, such as discriminant analyses, decision trees, and k-nearest neighbors' approaches provided greater than 75% accuracy in all cases. SVM methods provided relatively highest accuracy. In most cases, a significant classification overlap was noted in between glands and ducts. A potential explanation for this behavior might be volume averaging. Volume averaging can occur when a structure is only partly present within the voxel. The effect is exacerbated when finer structures are embedded within other structures such as the case of ducts inside glands. While both ducts and glands have relatively distinct range of speed of sound, the median and range of attenuation and reflection values are somewhat similar. Volume averaging can potentially affect all of the three modalities in both lateral and axial direction, and can confound the performance of our image intensity based classifier. A possible method to circumvent its effects is to employ shape-recognition based geometric information in addition to our intensity based classifier. For instance, assuming ducts are relatively continuous and 'connected' across axially adjacent images/slices, misclassification of ducts as glands can be potentially improved. This form of geometric information might also be embedded in second order statistics, such as gray level co-occurrence matrices.

A common artifact in ultrasound imaging is motion. While the effect of motion artifact is somewhat accounted for due to fast and repetitive imaging of a given region in conventional B-mode ultrasound, three-dimensional ultrasound embodiments do not typically allow imaging of the same region in such a continuous manner. Specifically, the motion artifact associated with patient movement in a pendant breast position can affect the image quality. However, utilizing a breast retention apparatus yields a relatively much steadier mechanism in comparison to a freely pendant breast position. In addition, the slight but gentle stretching of nipple can aid in decreasing the effective angle of incidence in the lower breast, resulting in more energy transmitted through the region and, hence, better image quality.

It should be understood that the examples and embodiments described herein are for illustrative purposes only and that various modifications or changes in light thereof will be suggested to persons skilled in the art and are to be included within the spirit and purview of this application.

What is claimed is:

1. A method of tissue type identification comprising:
   evaluating image data comprising at least a speed of sound image and a reflection image, wherein each pixel of at least the speed of sound image and the reflection image are co-registered, to assign a color to each pixel registration;
   distinguishing connective tissue and fat from each other, and from ducts and glands, using both speed of sound data and reflection data, wherein the connective tissue and the fat have speed of sound data greater than the ducts and the glands, and wherein the connective tissue have reflection data greater than the fat;
   storing for each pixel registration a color parameter indicating the assigned color for at least one of the connective tissue, the fat, the ducts, and the glands;
   in response to receiving a request to display a particular tissue type, identifying each pixel registration storing a corresponding color parameter for the particular tissue type; and
   displaying the assigned color for each pixel registration identified as storing the corresponding color parameter for the particular tissue type in a view screen.

2. The method of claim 1, further comprising: displaying an isolated tissue or tissues as based on a selected tissue type or color.

3. The method of claim 1, wherein storing the color parameter comprises replacing at least the speed of sound data and reflection data of the pixel registration with the color parameter.

4. The method of claim 1, wherein storing the color parameter comprises adding the color parameter to at least the speed of sound data and the reflection data of the pixel registration.

5. The method of claim 1 further comprising:
   distinguishing the ducts from the glands using speed of sound data.

6. The method of claim 1, wherein the image data further comprises an attenuation image co-registered with the speed of sound image and the reflection image.

7. The method of claim 6, wherein storing the color parameter comprises replacing at least the speed of sound data, the reflection data, and the attenuation data of the pixel registration with the color parameter.

8. The method of claim 6, wherein storing the color parameter comprises adding the color parameter to at least the speed of sound data, the reflection data, and the attenuation data of the pixel registration.

9. The method of claim 1, wherein distinguishing the tissue types utilizes a decision tree.

10. The method of claim 1, wherein distinguishing the tissue types utilizes a typing matrix.

11. The method of claim 1, further comprising:
    determining a first range of speed of sound values for the speed of sound image defining a fat sound condition;
    determining a second range of speed of sound values for the speed of sound image defining a connective tissue sound condition, wherein the second range of speed of sound values includes higher values than the first range of speed of sound values;
    determining a third range of speed of sound values for the speed of sound image defining a glands sound condition, wherein the third range of speed of sound values includes higher values than the second range of speed of sound values;
    determining a fourth range of speed of sound values for the speed of sound image defining a ducts condition, wherein the fourth range of speed of sound values includes higher values than the third range of speed of sound values;
    determining a first range of reflection values for a reflection image defining a fat reflection condition;
    determining a second range of reflection values for the reflection image defining a ducts reflection condition, wherein the second range of reflection values includes higher values than the first range of reflection values;
    determining a third range of reflection values for the reflection image defining a glands reflection condition, wherein the third range of reflection values includes higher values than the first range of reflection values;
    determining a fourth range of reflection values for the reflection image defining a connective tissue condition, wherein the fourth range of reflection values includes higher values than the third range of reflection values;
    combining at least the fat sound condition and the fat reflection condition to create a fat criteria;
    combining at least the glands sound condition and the glands reflection condition to create a glands criteria;
    combining at least the ducts sound condition and the ducts reflection condition to create a ducts criteria; and
    combining at least the connective tissue sound condition and the connective tissue reflection condition to create a connective tissue criteria.

12. The method of claim 11, further comprising:
    determining a first range of attenuation values for an attenuation image defining a glands attenuation condition;
    determining a second range of attenuation values for the attenuation image defining a ducts attenuation condition, wherein the second range of attenuation values includes higher values than the first range of attenuation values;
    determining a third range of attenuation values for the attenuation image defining a fat attenuation condition, wherein the third range of attenuation values includes higher values than the second range of attenuation values; and
    determining a fourth range of attenuation values for the attenuation image defining a connective tissue condition, wherein the fourth range of attenuation values includes higher values than the third range of attenuation values.

13. The method of claim 12, further comprising:
    combining the fat sound condition, the fat reflection condition, and the fat attenuation condition to create the fat criteria;
    combining the glands sound condition, the glands reflection condition, and the glands attenuation condition to create the glands criteria;
    combining the ducts sound condition, the ducts reflection condition, and the ducts attenuation condition to create the ducts criteria; and
    combining the connective tissue sound condition, the connective tissue reflection condition, and the connective tissue attenuation condition to create the connective tissue criteria.

14. The method of claim 1, further comprising:
    in response to receiving a request remove a particular tissue type, identifying each pixel registration storing a corresponding color parameter for the particular tissue type; and removing the assigned color for each pixel registration identified as storing the corresponding color parameter for the particular tissue type from the view screen.

15. The method of claim 1, further comprising:

in response to receiving a request remove a particular tissue type, identifying each pixel registration storing a corresponding color parameter for the particular tissue type; and removing the assigned color for each pixel registration identified as storing the corresponding color parameter for the particular tissue type from the view screen.

16. The method of claim 1, further comprising:

utilizing at least one of a linear support vector machine, radial basis function support vector machine with a Gaussian kernel, nonparametric Mann-Whitney U-test, Holm correction, discriminant analysis, decision tree, and k-nearest neighbors in assigning the color.

17. The method of claim 1, the method further comprising:

employing shape-recognition based geometric information to distinguish glands from ducts and classifying the pixels as ducts or maintaining the pixel as glands based on the outcome of employing shape-recognition based geometric information.

* * * * *